United States Patent [19]

Bergersen

[11] Patent Number: 4,764,112

[45] Date of Patent: Aug. 16, 1988

[54] MOLDED DISTAL STOP AND ATTACHMENT TO FIX ORTHODONTIC APPLIANCE INTO MOUTH

[76] Inventor: Earl O. Bergersen, 950 Green Bay Rd., Winnetka, Ill. 60093

[21] Appl. No.: 107,167

[22] Filed: Oct. 13, 1987

[51] Int. Cl.⁴ ............................................. A61C 7/00
[52] U.S. Cl. ....................................... 433/22; 433/20
[58] Field of Search ........................ 433/11, 17, 20, 22

[56] References Cited

U.S. PATENT DOCUMENTS 3,987,547 10/1976 Moss .................................... 433/20
3,997,970 12/1976 Hodgson ............................. 433/20

Primary Examiner—Robert Peshock
Attorney, Agent, or Firm—Hill, Van Santen, Steadman & Simpson

[57] ABSTRACT

An attachment arrangement for an orthodontic appliance is provided in which a stop covering is secured on an arch-wire appliance so that the covering will abut against a mesial end of the buccal tubes to which the wire is attached. The covering includes an elastic tab part which has an opening therethrough to engage over an end of the wire behind the buccal tube so that the tube is clamped between an anterior part of the covering and the tab end. The covering can be trimmed to remove a posterior portion thereof to permit the wire to move distally within the mouth and spacers can be inserted onto the wire to be positioned between the covering and the tube to move the wire mesially. The elastic tab permits quick removal and replacement of the appliance.

8 Claims, 1 Drawing Sheet

MOLDED DISTAL STOP AND ATTACHMENT TO FIX ORTHODONTIC APPLIANCE INTO MOUTH

BACKGROUND OF THE INVENTION

1. Field of the Invention

The present invention relates to orthodontic devices and more particularly to an attachment arrangement for arch-wires or head-gear to the mouth.

2. Description of the Prior Art

Orthodontic appliances in the form of arch-wire or head-gear are commonly used during orthodontic treatments to move various teeth within the mouth to certain desired locations. In order to move the teeth, the wires must be securely attached to the teeth and this is generally accomplished by applying bands to the teeth and then attaching the wires to the bands. In the past, the wires are permanently attached to the bands, such as by soldering which makes removal or adjustment of the wires very difficult and time consuming.

The wires generally are provided with loops formed therein to permit some measure of adjustment in the configuration of the wire as the teeth move, however such adjustments also are time consuming and must be done with a great deal of precision in order to maintain a proper fit of the wire within the mouth.

SUMMARY OF THE INVENTION

The present invention provides for an improved means for attaching an orthodontic appliance such as an arch-wire or head-gear wire to the teeth within the mouth, this attachment means permitting relatively easy removal of the wire from the teeth as well as easy position adjustability of the wire without readjusting the configuration of the wire.

More particularly, the present invention provides a molded stop covering which is molded onto the wire and generally is in the form of a cylinder formed around the wire. Since the wires are attached to the teeth by passing through buccal tubes formed on tooth bands or through buccal tubes secured directly to the teeth,, the stop covering is formed with a diameter large enough to prevent its passage through the tube. The stop covering can be trimmed to a desired length so that the most distal end of the covering rubs or abuts against the mesial end of the buccal tube preventing the wire from moving further back into the tube, and thereby fixes or stabilizes the wire at that position.

A connector tab is integrally molded with the stop covering and is an extension of thin diameter flexible material which extends from the mesial section of the stop covering. The connector tab has a small diameter hole in an end portion thereof and the tab can be stretched between its connection point with the stop covering and the hole. When the wire is positioned correctly in the buccal tube and the distal end of the stop abuts against the mesial end of the tube, a distal end of the wire sticks out through the distal end of the tube. The tab can be stretched and the opening at the end of the tab placed over the protruding wire end such that when the stretching force on the tab is released, the tab will retain the wire within the tube.

As treatment continues, the posterior teeth are pushed in a distal direction and thus adjustment of the positioning of the wire relative to the buccal tube must be accommodated. This procedure is very easily accomplished in accordance with the invention by restretching the tab to release the tab from the distal end of the wire, pulling the wire out of engagement with the tube and placing an annular spacer on the wire which will abut against the distal end of the spacer and will then engage the mesial end of the buccal tube so that the entire wire structure will be moved forwardly to accommodate the rearward movement of the teeth. The tab can then be restretched and reattached to the distal end of the wire so that the wire will again be securely held in place relative to the teeth.

Due to the easy connection and repositioning of the wire, the previously required steps of either breaking the solder connections and resoldering or readjusting the configuration of the wire are not required thereby greatly reducing the time and effort involved in these steps.

DESCRIPTION OF THE PREFERRED EMBODIMENTS

Figure 1:
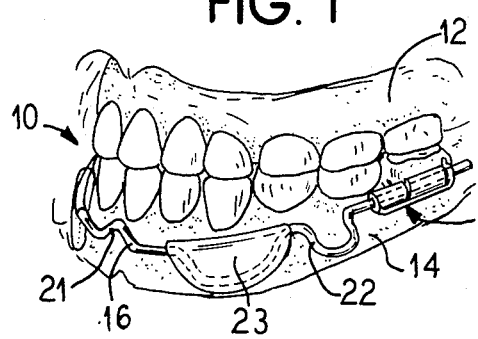
FIG. 1 is a perspective view of an arch wire connected to a lower set of teeth.

FIG. 1 illustrates a perspective view of a human jaw 10 including an upper jaw 12 and a lower jaw 14. During orthodontic treatment it is oftentimes necessary to move the posterior teeth rearwardly in order to open up space for crowded anterior teeth and to accomplish this it is known to use such orthodontic appliances as arch-wires, bumpers, or head-gear.

Figure 2:
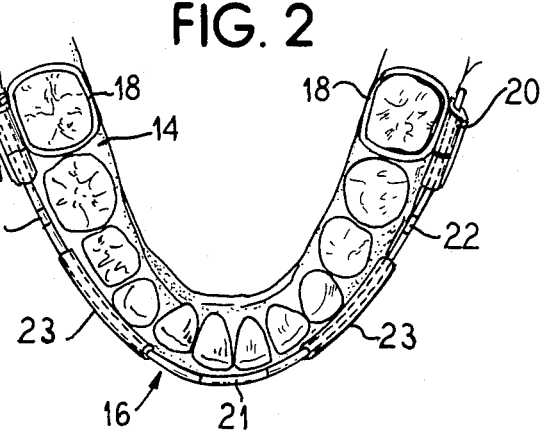
FIG. 2 is an occlusal view of the attached wire illustrated in FIG. 1.
Figure 3:
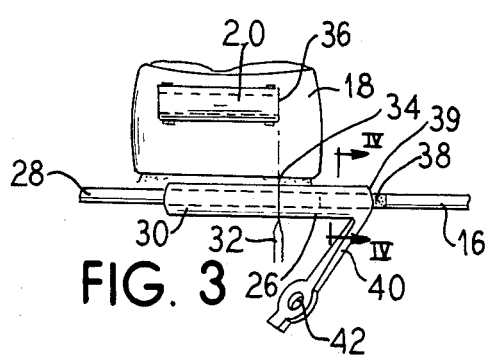
FIG. 3 is a buccal side elevational view of a molar band and the wire during a trimming step.
Figure 4:
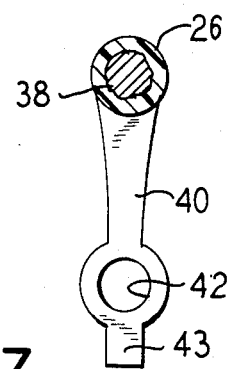
FIG. 4 is a sectional view through the wire and the molded covering and tab.

An arch-wire 16 is illustrated in FIGS. 1 and 2 as being applied to the lower jaw 14. The arch-wire could also be attached to the upper jaw or there could be such a wire attachment to both the upper and lower jaws. A head gear includes an arch-wire as illustrated and further includes a band encircling the posterior side of the head to provide additional distal drive to the posterior teeth. One such device is illustrated in my prior U.S. Pat. No. 4,330,272. Generally, the application of the arch-wire to the teeth includes the placement of an encircling band 18 applied to a pair of posterior teeth such as the first or second molars, one band being placed on each lateral side of the mouth. The band 18 has permanently attached thereto a buccal tube 20 which receives an end of the wire 16. Alternatively, the buccal tube may be attached directly to the tooth by an epoxy, or the tube may be attached to another appliance such as illustrated in my identified patent.

The wire 16 illustrated in FIGS. 1 and 2 includes an anterior central loop 21 and a pair of side loops 22 to permit the wire to be conformed to the configuration of the patient's jaw. The wire also generally includes a pair of laterally spaced bumpers 23 which are molded directly onto the wire and which are engaged by the patient's lips to provide a rearward or distal pressure on the wire which will force the teeth to move distally as desired.

An attachment means 24 is provided in accordance with the principles of the present invention which permits the wire 16 to be easily secured to, removed from and repositioned relative to the buccal tubes 20 to which the wire 16 is to be connected. This attachment means 24 is illustrated in greater detail in FIGS. 3-9 where it is seen that the attachment means comprises a molded covering 26 which is generally cylindrical in shape and which covers a length of the wire just anterior to a free posterior or distal end 28 of the wire. The covering 26 preferably has a diameter approximately the same as that of the buccal tube 20, but in any event should be sufficiently large to prevent the covering 26 from entering into the tube 20.

Once the wire 16 has been adjusted in configuration to fit the patient, the wire can be put in place along side the tube 20 and a distal or posterior portion 30 of the covering 26 can be trimmed away by a knife 32 (FIG. 3) so that a remaining distal end 34 of the covering 26 will abut against a mesial end 36 of the tube to provide the proper front to back spacing of the wire relative to the tube 20.

Figure 5:
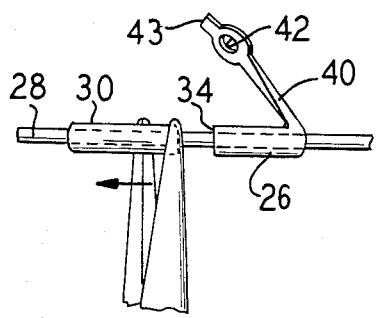
FIG. 5 illustrates the step of removing the trimmed portion of the stop covering.

The wire 16 preferably has roughened outer surface section 38 (FIGS. 3 and 4) underlying a mesial or posterior end 39 of the covering 26 to ensure that the covering 26 will not slide on the wire. The distal portion 30 of the covering preferably overlies a smooth outer surface of the wire 16 and thus is more easily removed from the wire 16 after trimming by the knife 32 as is illustrated in FIG. 5. Alternatively, the covering 26 could be formed separately from the wire and could be secured to the wire by appropriate fastening means such as by epoxy which might require little or no trimming.

The covering 26 includes an elongated tab 40 extending from the mesial end 39 of the covering and which includes an opening 42 therethrough near a free end 43, sized to receive the free end 28 of the wire 16. The covering and tab can be molded integrally at the same time onto the wire and the tab comprises a thin diameter flexible and resilient material.

Figure 7:
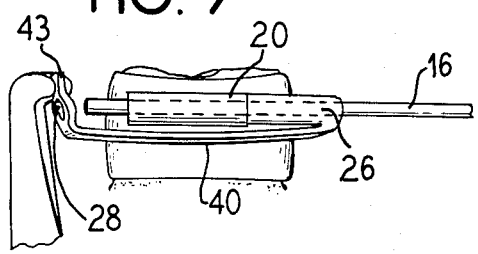
FIG. 7 illustrates the step of securing the wire to the tube by use of the tab.
Figure 6:
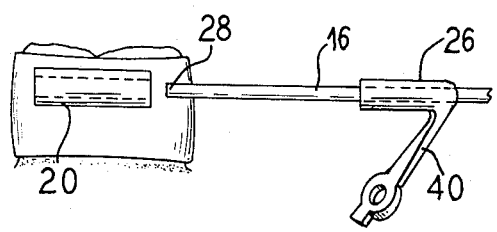
FIG. 6 is a view of the step of inserting the wire into the buccal tube.
Figure 8:
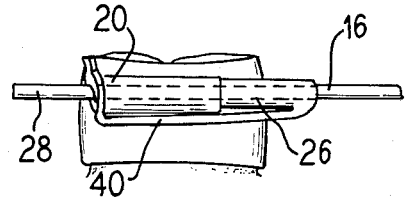
FIG. 8 illustrates the assembled position of the wire and buccal tube.

After the distal portion of the covering is removed, the wire is positioned correctly in the tube 20 and the tab 40 is stretched distally by grasping the free end 43 so that the opening 42 can be placed over the free end 28 of the wire as illustrated in FIG. 7. Then the stretching force on the tab is released causing the tab 40 to contract thereby clamping the wire 16 to the tube 20 as illustrated in FIG. 8. Thus the distal end 34 of the covering 26 will abut against the mesial end 36 of the tube 20 such that rearward pressure of the wire 16 will be transmitted to the tooth through the engagement of the covering 26 with the tube 20.

Figure 9:
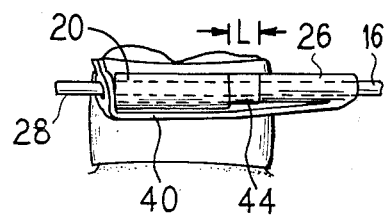
FIG. 9 illustrates the use of an additional spacer when repositioning the wire relative to the tube.

As the treatment continues, the posterior teeth will move distally and as this occurs, it is necessary to reposition the wire 16 relative to the connecting tubes 20 to provide continued rearward pressure on the teeth. This is easily accomplished by use of the connection means of the present invention by restretching the tab 40 to release the tab from the end of the wire, removing the wire from the tube 20, placing an annular spacer 44 onto the distal end of the wire and sliding it up to engagement with the distal end 34 of the covering 26 to in effect elongate the covering. An axial length L of the spacer is selected to provide the desired degree of distal repositioning of the wire 16 relative to the tube 20. The distal end 28 of the wire is reinserted into the tube 20 and the tab 40 is stretched to insert the wire end 28 through the tab opening 42 to again provide a clamping attachment of the wire to the tube with the interposed spacer 44 as illustrated in FIG. 9.

In this manner, the wire can be quickly removed and repositioned relative to the teeth without requiring that the wire 16 be reconfigured and without requiring labor intensive disconnective and reconnective procedures.

While the abutment of the covering 26 with the tube 20 prevents any appreciable movement of the wire 16 rearwardly with respect to the tubes 20, the elastic nature of the tab 40 does permit the user to pull the wire 16 forwardly to a limited degree to assist in cleaning of the teeth. Further, although the connecting means is sufficiently strong to normally remain securely attached to the wire, it is possible to disengage the wire from the teeth in emergency situations by a forceful forward pulling on the wire thereby permitting relatively quick and easy removal of the appliance from a patient's mouth in the case of an emergency such as a facial injury. This would not be possible in the case of more permanently secured appliances.

Thus, the invention provides an elastic clamping arrangement fixed to the wire having a first part which abuts against the mesial end of the buccal tube, a second part which abuts against the distal end of the tube and an elastic part connecting the first and second parts to provide a clamping action therebetween. A third part may also be placed on the wire to space the first part from the mesial end of the tube.

As is apparent from the foregoing specification, the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

I claim as my invention:

1. An attachment means for an orthodontic appliance wherein the appliance includes an arch-wire having a generally U-shaped configuration with two free posterior ends each to be inserted through an opening in a mesial end of a separate buccal tube comprising:

a covering formed on each lateral side of said wire having a posterior end positioned anterior to said posterior end of said wire to abut against said mesial end of said tube and an anterior end including an integrally formed resilient tab, said tab including an opening therethrough sized to receive said posterior wire end.

2. An attachment means according to claim 1, wherein said anterior end of said covering is securely attached to said wire and said posterior end of said covering is removably attached to said wire whereby said anterior end of said covering can be selectively trimmed and removed from said wire to reduce the length of the covering.

3. An attachment means according to claim 2, wherein said wire is roughened in an area underlying said anterior end to provide said secure attachment of said end to said wire.

4. An attachment means according to claim 1, including an annular spacer member with a central opening sized to receive said posterior end of said wire to permit said spacer to abut against said posterior end of said covering.

5. An attachment means for an orthodontic appliance wherein the appliance includes an arch-wire having a generally U-shaped configuration with two free posterior ends each to be inserted through an opening in a mesial end of a separate buccal tube to protrude from a distal end of the tube comprising:
an elastic clamping arrangement fixed to said wire having a first part which abuts against said mesial end of said buccal tube, a second part which abuts against said distal end of said buccal tube and an elastic part connecting said first and second parts to provide a clamping action therebetween.

6. An attachment means according to claim 5, wherein said first part is secured to said wire and said second part has an opening therethrough for selectively receiving said posterior end of said wire.

7. An attachment means according to claim 5, wherein said first part, said second part and said elastic part are integrally formed in a single molding process.

8. An attachment means according to claim 5, including a third part positioned on said wire between said first part and said buccal tube.

* * * * *